(12) United States Patent
Sainath et al.

(10) Patent No.: US 7,283,605 B2
(45) Date of Patent: Oct. 16, 2007

(54) METHODS AND APPARATUS FOR SCATTER CORRECTION

(75) Inventors: Paavana Sainath, Oconomowoc, WI (US); Xiaoye Wu, Rexford, NY (US); Masatake Nukui, Tokyo (JP); Ronald Joseph Lundgren, Lisbon, WI (US); Thomas John Myers, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/331,727

(22) Filed: Jan. 14, 2006

(65) Prior Publication Data

US 2007/0165772 A1    Jul. 19, 2007

(51) Int. Cl.
   *H05G 1/60*    (2006.01)
(52) U.S. Cl. .................. 378/7; 378/86; 378/207; 378/210; 378/901
(58) Field of Classification Search ............ 378/19, 378/6, 7, 210, 901
   See application file for complete search history.

(56) References Cited

U.S. PATENT DOCUMENTS

| 4,580,219 | A  | * | 4/1986  | Pelc et al.      | 382/131   |
|-----------|----|---|---------|------------------|-----------|
| 4,985,906 | A  |   | 1/1991  | Arnold           | 378/18    |
| 5,099,505 | A  | * | 3/1992  | Seppi et al.     | 378/65    |
| 5,165,100 | A  | * | 11/1992 | Hsieh et al.     | 382/131   |
| 5,412,563 | A  |   | 5/1995  | Cline et al.     | 364/413.22|
| 5,644,612 | A  | * | 7/1997  | Moorman et al.   | 378/98.2  |
| 5,970,112 | A  | * | 10/1999 | Hsieh            | 378/8     |
| 6,618,466 | B1 | * | 9/2003  | Ning             | 378/62    |
| 6,639,964 | B2 |   | 10/2003 | Schneider et al. | 378/7     |
| 6,687,326 | B1 | * | 2/2004  | Bechwati et al.  | 378/7     |
| 6,778,637 | B2 |   | 8/2004  | Luhta et al.     | 378/154   |
| 2005/0276373 | A1 | * | 12/2005 | Ying et al.   | 378/7     |
| 2006/0008046 | A1 | * | 1/2006  | Ruhrnschopf   | 378/7     |
| 2006/0153328 | A1 | * | 7/2006  | Schlomka et al. | 378/4   |

* cited by examiner

*Primary Examiner*—Courtney Thomas
*Assistant Examiner*—Alexander Taningco
(74) *Attorney, Agent, or Firm*—Fisher Patent Group, LLC; Thomas M. Fisher

(57) ABSTRACT

A method for reconstructing an image of an object includes scanning the object with a computed tomography (CT) system to obtain data, estimating a size of the object using the obtained data, using the estimated size of the object to perform scatter correction on the obtained data, and reconstructing an image using the scatter corrected data.

17 Claims, 6 Drawing Sheets

METHODS AND APPARATUS FOR SCATTER CORRECTION

BACKGROUND OF THE INVENTION

This invention relates generally to methods and apparatus for computed tomography (CT), and more particularly to methods and apparatus that provide for 3D scatter correction.

Cone Beam Multi-Slice Computed Tomography (CT) Systems have wider Z-Axis coverage than traditional MultiDetector CT systems (MDCT). The traditional MDCT systems were limited to beam widths of 20 mm or lower. With the advent of Cone Beam Multi-Slice systems, the new beam width is more than double the beam width of traditional MDCT systems. These new systems are typically more sensitive to the effect of scattered radiation (scatter). Scatter can be described as spurious radiation due to X-rays bouncing off the internal components of the CT system or the object being scanned. The effective correction for scatter is more important when the CT detector is not effectively collimated to reject scattered radiation.

Scatter causes dark shading artifacts and CT Number non-uniformity in the objects being scanned, as well as a CT Number accuracy dependence on object size and aperture width. Very low frequency scatter profile adds a positive bias to the detected radiation signal, thus reducing the effective attenuation of the imaged object, resulting in a negative bias in the measured Hounsfield Units (HU) in images. Coupled with highly varying attenuation profiles of the object being imaged, scatter can cause differential artifacts, such as shading in uniform regions.

Accordingly, it would be desirous to reduce or eliminate the effects of scatter. Therefore, 3D scatter correction methods and apparatus are described below.

BRIEF DESCRIPTION OF THE INVENTION

In one aspect, a method for reconstructing an image of an object is provided. The method includes scanning the object with a computed tomography (CT) system to obtain data, estimating a size of the object using the obtained data, using the estimated size of the object to perform scatter correction on the obtained data, and reconstructing an image using the scatter corrected data.

In another aspect, a cone beam computed tomography (CT) system is provided. The system includes a radiation source configured to emit a cone beam of radiation, a detector positioned to receive the cone beam, and a computer coupled to the source and detector. The computer is configured to receive data from the detector, estimate a size of an object using the received data, perform scatter correction on the received data using the estimated size of the object, and reconstruct an image using the scatter corrected data.

In still another aspect, a computer readable medium embedded with a program is provided. The program is configured to instruct a computer to receive data from a detector, estimate a size of an object using the received data, and perform scatter correction on the received data using the estimated size of the object.

In still another aspect, a computer readable medium embedded with a program is provided wherein the program is configured to instruct a computer to receive a bowtie filter type and estimate a detector scatter profile using the received filter type.

In still another aspect, a computer readable medium embedded with a program is provided wherein the program is configured to instruct a computer to z-weight a detector scatter profile to obtain a plurality of row scatter profiles.

DETAILED DESCRIPTION OF THE INVENTION

Figure 1:
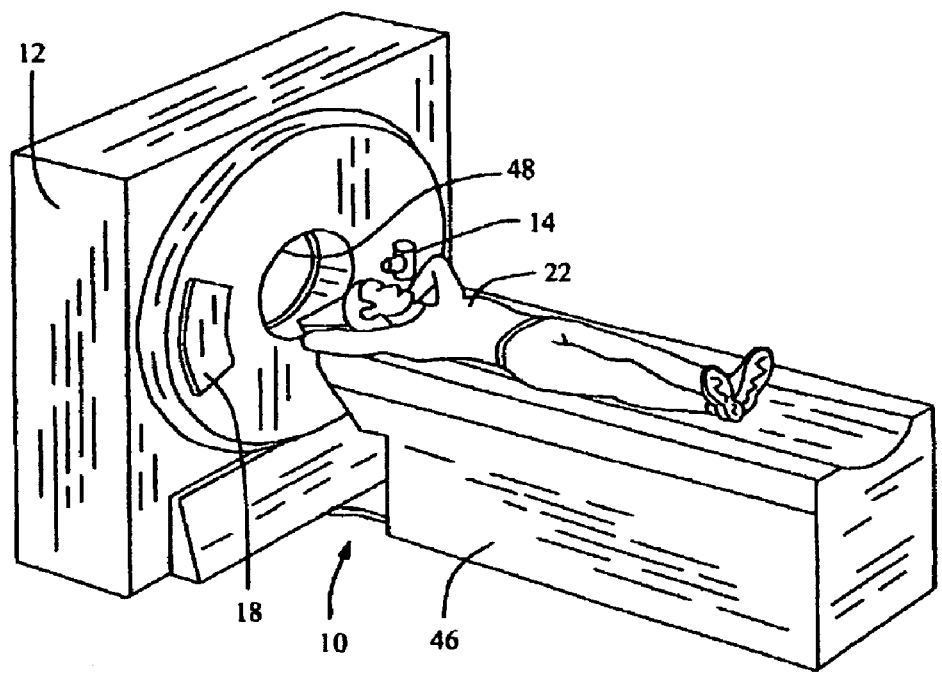
FIG. 1 is a pictorial view of a CT imaging system embodiment.

There are herein provided scatter correction methods and apparatus useful for imaging systems such as, for example, but not limited to a Computed Tomography (CT) System. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 2:
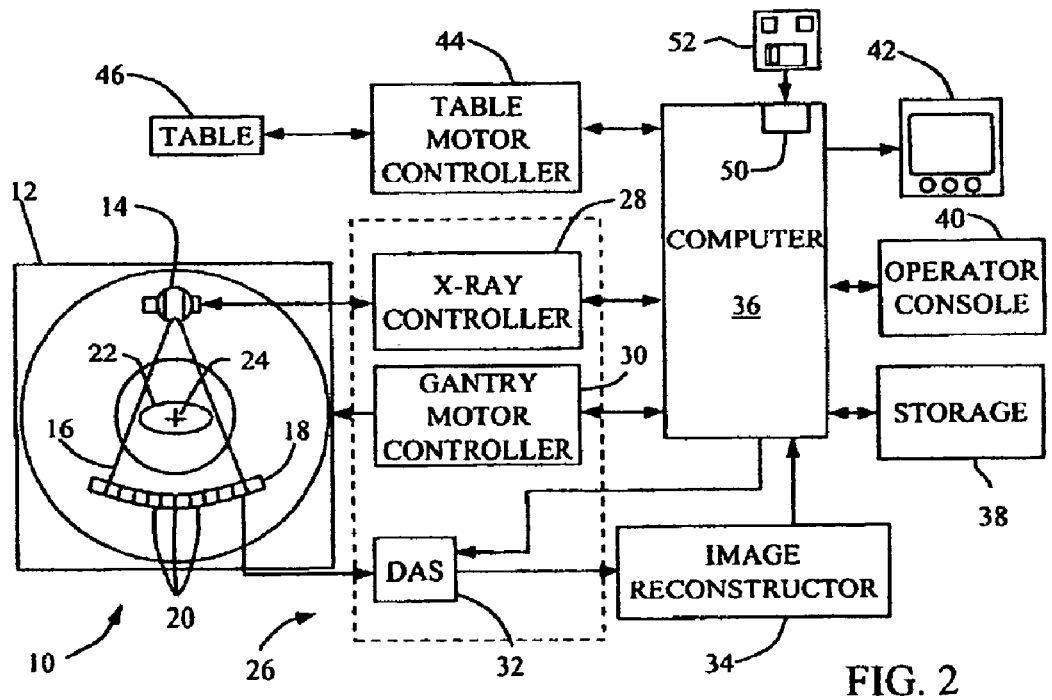
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system Gantry 12 has a radiation source 14 that projects a cone beam 16 of X-rays toward a detector array 18 on the opposite side of gantry 12.

Detector array 18 is formed by a plurality of detector rows (not shown in FIGS. 1 and 2) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via a console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

In one embodiment, CT system 10 is a Cone Beam Multi-Slice Computed Tomography (CT) System 10 in that radiation source 14 is configured to provide a Cone Beam of x-rays through object 22 and onto multislice detector array 18.

Cone Beam Multi-Slice Computed Tomography (CT) Systems have wider Z-Axis coverage than traditional MultiDetector CT systems (MDCT). The traditional MDCT systems were limited to beam widths of 20 mm or lower. With the advent of Cone Beam Multi-Slice systems, the beam width is more than double the beam width of traditional MDCT systems. These systems are typically more sensitive to the effects scatter.

Scatter causes dark shading artifacts and CT Number non-uniformity in the objects being scanned, as well as a CT Number accuracy dependence on object size and aperture width. Very low frequency scatter profile adds a positive bias to the detected radiation signal, thus reducing the effective attenuation of the imaged object, resulting in a negative bias in the measured Hounsfield Units (HU) in images. Coupled with highly varying attenuation profiles of the object being imaged, scatter can cause differential artifact, such as shading in uniform regions.

However, Cone Beam Multi-Slice Computed Tomography System 10 is configured as described below and provides for increased imaging capabilities over known Cone Beam Multi-Slice Computed Tomography Systems. System 10 is configured to perform a 3D scatter correction. It has been found that the scattered radiation in any given row is dependent on the beam width, kVp, bowtie filter and the size of the object being scanned. It has also been found that scatter is approximately proportional to the square root of the raw projection data after the dark current is subtracted and the data is normalized to the reference channels. Therefore, in one embodiment, the scatter estimate is the square root of the raw projection data after the dark current is subtracted and the data is normalized to the reference channels. Normalizing the channel to channel detector gain differences (hi-frequency content) out of the data without removing the shape of the bowtie filter (which is a significant contributor to the overall scatter profile) has been shown to be useful in performing the scatter correction. Therefore, in one embodiment, the detector gain differences are removed prior to performing the correction. Because known post-processing algorithms are already used to account for the detector gain differences, one embodiment re-introduces the previously removed detector gain differences such that no programming changes are needed while still performing the herein described scatter correction.

It has also been found that the size of the object being scanned can be computed as an integral of the negative logarithm treated uncorrected projections. Therefore, one embodiment uses that integral as a size estimate. The size estimate can be computed once per rotation, and for each detector row in the axial scan mode.

After estimating the size of the object, a polynomial relationship can be derived between the scaling factor for the scatter profile and the estimated size of the object. This relationship can be characterized as a function of varying object size and attenuation for each combination for kVp, bowtie filter, and aperture size. In other words, an integral is used to estimate the size based on the negative logarithm treated raw data, and the square root of the raw data is used as a scatter estimate, and then the estimated size is correlated to the estimated scatter in a polynomial to obtain a scaling factor. The scaling factor can then be used to scale the estimated scatter profile (square root of the raw data). Also, the scatter profile for each detector row can then be derived as a weighted sum of the scatter from all the detector rows in the data. Therefore, as used herein the term "detector scatter profile" refers to the scatter profile of the entire detector, and the term "row scatter profile" refers to a profile for a specific row.

Finally, after the scatter profile for each detector row is computed, the scatter profile is smoothed such that only the low frequency effect is captured. As used herein the term low frequency refers to data representing a gradual varying function across at least ten channels, and the term high frequency refers to data representing a quickly varying function such as for every detector channel or every other detector channel. This profile is then subtracted from the raw projections to obtain scatter corrected data The detector gains (channel to channel gain variations) are then re-introduced into the data so that the rest of the data pre-processing can follow normally. The resulting scatter corrected data is then used in a conventional manner to reconstruct an image. As seen below, a scatter corrected image is superior to an image with out scatter correction During the above process, at various steps, the view angles and detector pixels in X can be decimated to improve computational speed, because the scatter profile is relatively smooth in nature.

Figure 3:
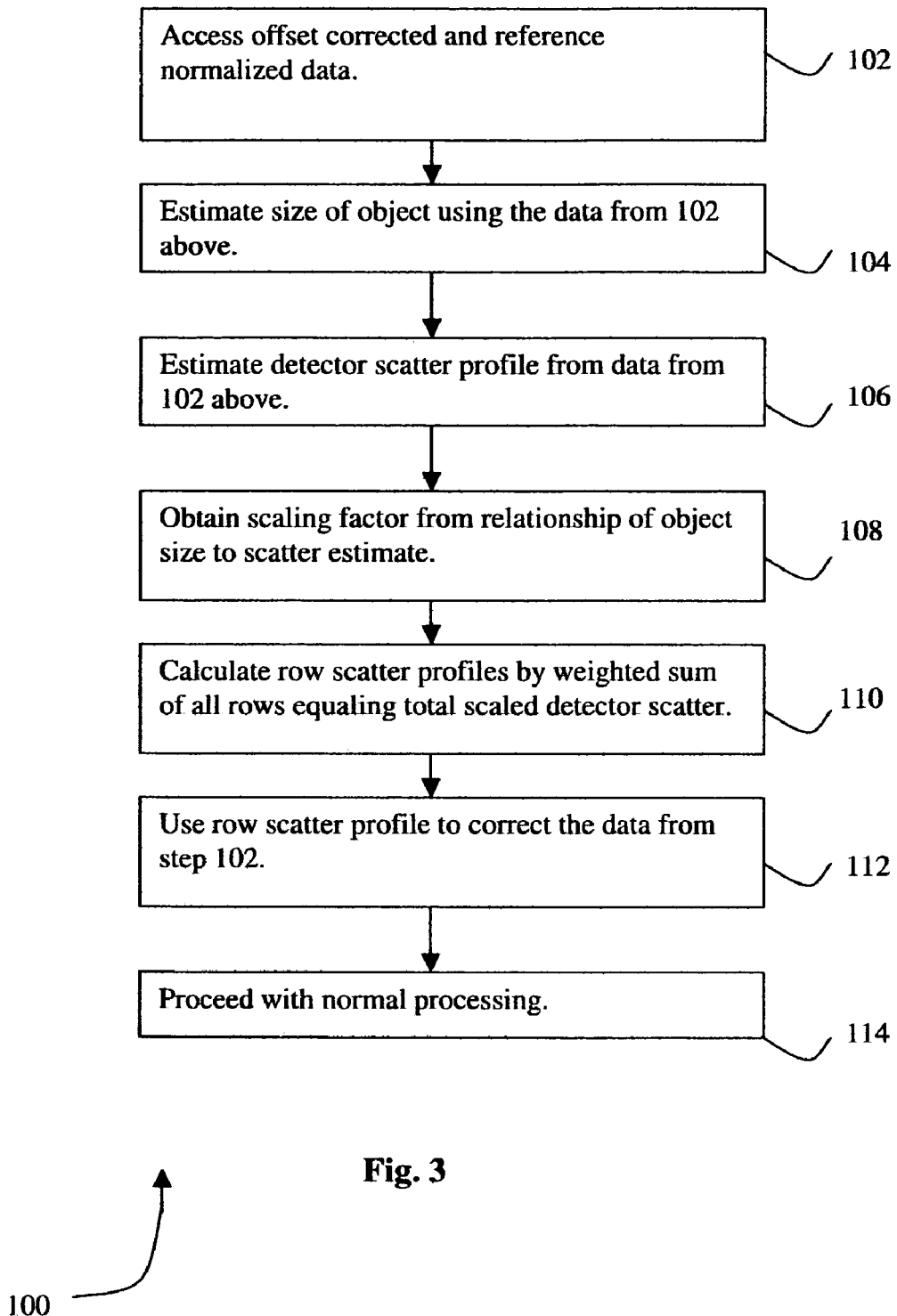
FIG. 3 illustrates a method for correcting scatter.

FIG. 3 illustrates a method 100 including accessing 102 offset corrected and reference normalized data, estimating 104 a size of an object using the accessed data, and estimating 106 a detector scatter profile from the accessed data.

Method 100 could include doing the offset correction and the reference normalization because it does not matter how the raw data is obtained. Additionally, although described as if the size is estimated first and the scatter profile is estimated second, there is no temporal requirement, and step 106 can be done prior to step 104. In one embodiment, not all channels are used. For example, in one embodiment, for all 64 rows of a 64-row detector (or all 32 rows for a 32-row detector), for one view, every fifth channel is used and interpolation is done later to obtain scatter profiles for all channels for all rows. Alternatively, all channels can be used and no interpolation is needed. Either way, the summation is to compute the sum [s(row)] of −log(data*acal vector). At step 106, for every row, system 10 computes SQRT(data). All channels may be used or less than all can be used. For example, in one embodiment, every 12th channel is used, and in another embodiment, every 7th channel is used. Additionally, because it is useful to preserve the effects of using a bowtie filter, in one embodiment, a user enters into system 10 the type of bowtie filter used and system 10 computes SQRT(data) based upon the bowtie type filter. For example, every 12th channel is used when a body bowtie filter was used for the scan and every 7th channel is used when a head bowtie was used for the scan. Alternatively, the user can enter a number for how many channels should be used. For example, the user enters five for every fifth channel or ten for every tenth channel.

Method 100 also includes obtaining 108 scaling factors from the relationship between the object size and the scatter profile. For example, a third order polynomial of s(row) is derived to obtain a scaling factor based on the step 106 result of sqrt(data) by multiplying the values of sqrt(data) on a row by row basis. This scaling factor is then used to scale the estimated scatter (sqrt(data)) to obtain a scaled total detector scatter profile.

At step 110, row scatter profiles are calculated by using a weighted sum of all the rows to equal the scaled total detector scatter. Because each row has scatter contribution from all rows in Z, the scaled total detector scatter will be a weighted sum of all 64 rows. In one embodiment, the weighting factor for each row is predetermined. Each row scatter profile is then subtracted from that row's data to correct scatter at step 112. The scatter corrected data is then ready for normal processing at step 114. In one embodiment, the scatter correction is limited to a maximum scatter-to-primary energy fluence ratio (SPR) so the corrected data remains positive.

Figure 4:
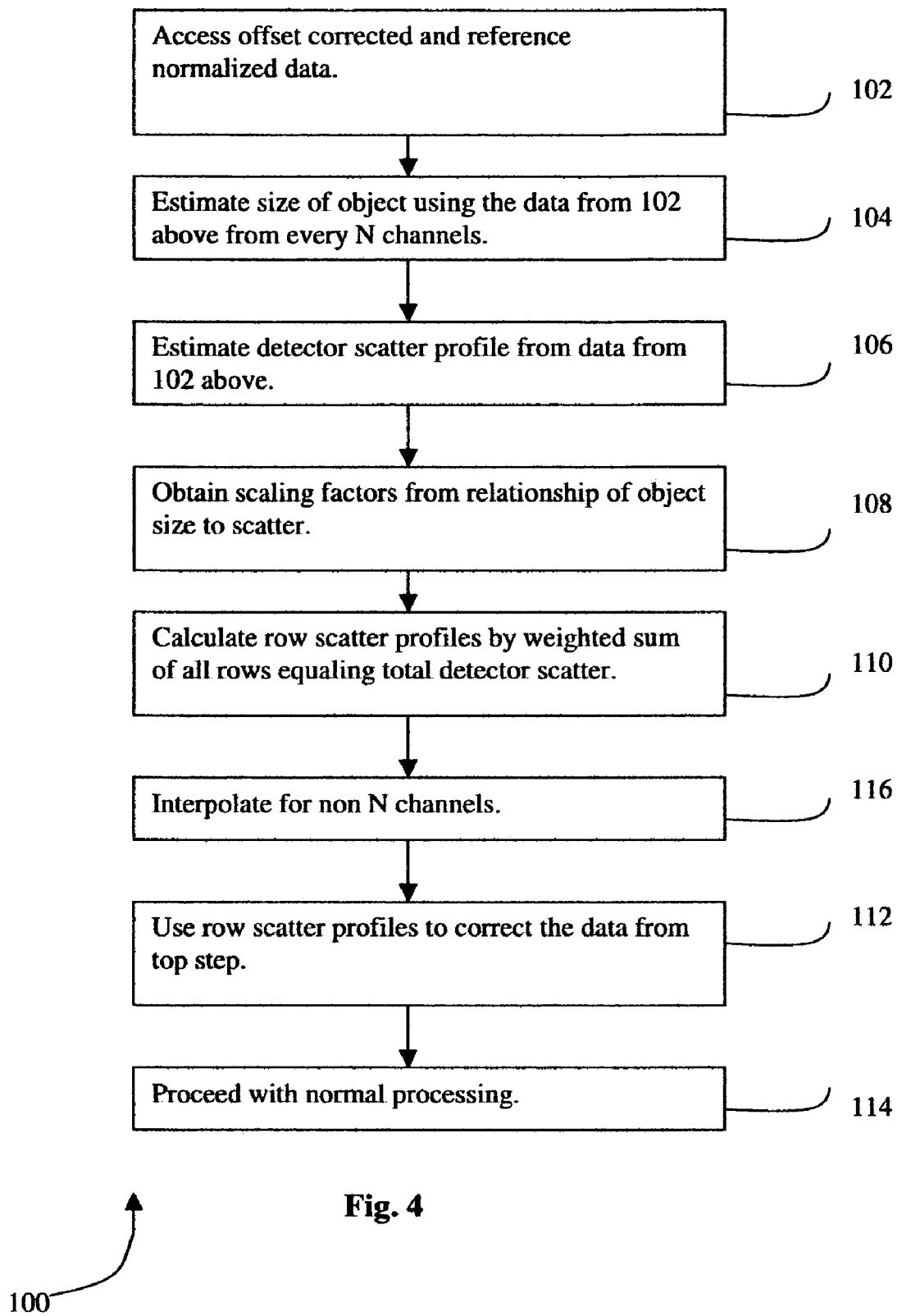
FIG. 4 illustrates a method for correcting scatter.

FIG. 4 illustrates the method 100, wherein step 104 includes estimating the size of an object from every N channels instead of every channel, and method 100 includes interpolating 116 for non N channels so the row profile is complete. In one embodiment, the user enters the N. In other embodiments, the N is pre-selected and not changeable by the user.

Figure 5:
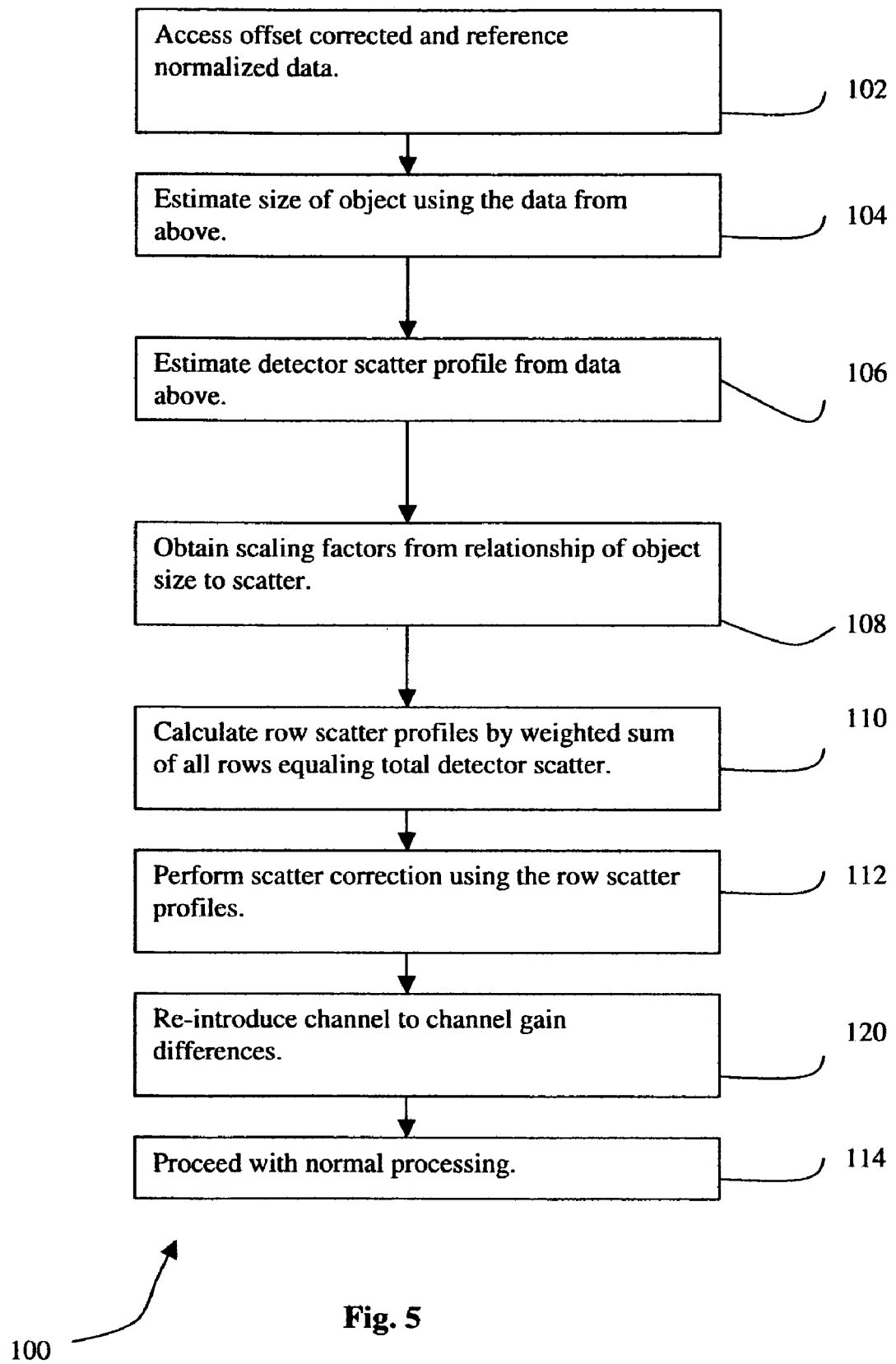
FIG. 5 illustrates a method for correcting scatter.

FIG. 5 illustrates method 100 with additional step of 120. Step 120 re-introduces the channel to channel gain differences. Step 120 allows for using conventional normal processing at step 114.

Figure 6:
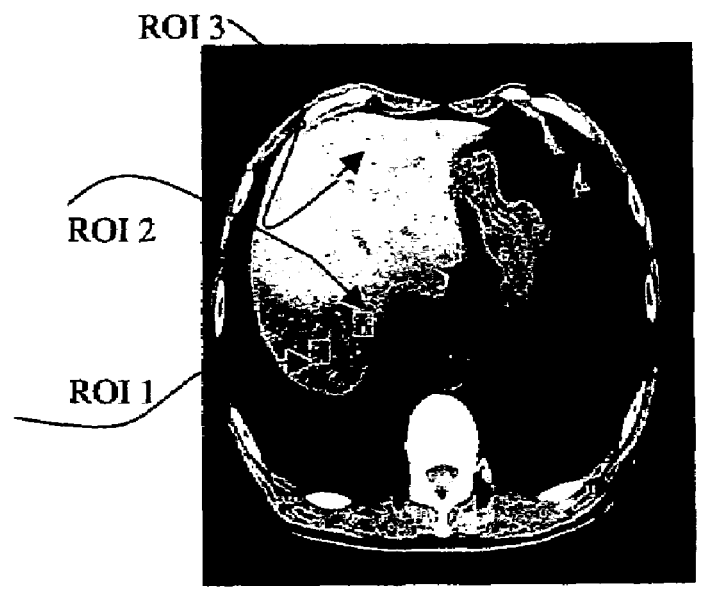
FIG. 6 illustrates a un-scatter corrected image.

FIG. 6 illustrates a un-scatter corrected image. Note the scatter at regions of interest (ROI) 1, 2, and 3 in a liver. The variance in CT numbers is 30 HU in these regions due to scatter.

Figure 7:
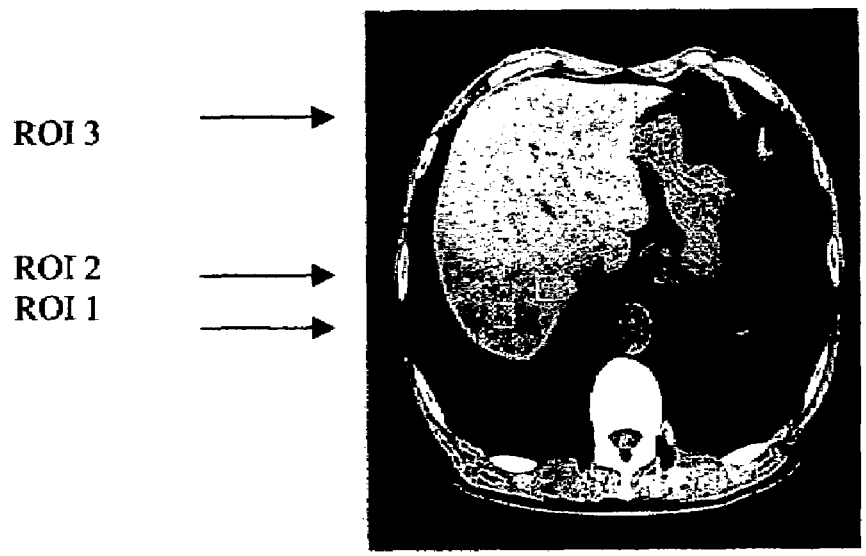
FIG. 7 illustrates the image from FIG. 6 with scatter correction.

FIG. 7 illustrates the image from FIG. 6 with the herein described scatter correction. The CT number variance in ROI 1, ROI 2, and ROI 3 is now about 15 HU. The CT number non-uniformity of FIG. 6 is considerably improved with the herein described 3D scatter correction as seen in FIG. 7.

Figure 8:
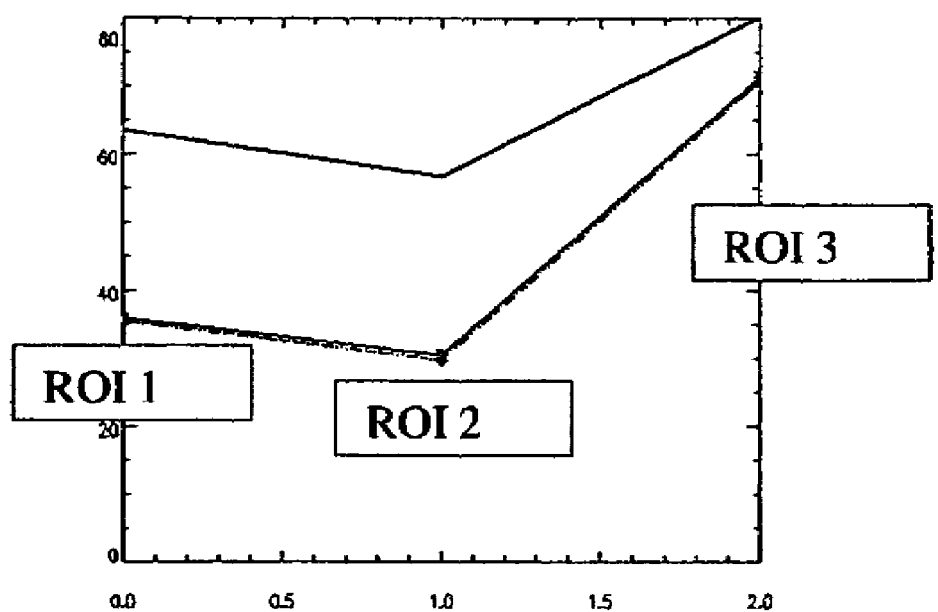
FIG. 8 illustrates the difference between CT number uniformity between the images of FIGS. 6 and 7.

FIG. 8 illustrates the difference between CT number uniformity between the images of FIGS. 6 and 7. In FIG. 8, the ordinate is the absolute CT number (pixel mean values), and the abscissa is for ROI 1, ROI 2, and ROI 3, with the bottom plot relating to FIG. 6 (uncorrected) and the top plot relating to FIG. 7 (scatter corrected). Note that in both plots ROI 2 is the lowest point and ROI 3 is the highest point, so for both plots the greatest CT number difference is between ROI 3 and ROI 2. The bottom plot represents a 30 HU difference while the top plot represents a 15 HU difference. Therefore, the herein described 3D scatter correction has resulted in a 50 percent improvement in CT number uniformity in a liver image.

The herein described methods and apparatus provides for a 3D scatter correction that better corrects for the Image Quality degradation due to scatter effects from anatomy changing rapidly in the Z-direction. This difference is due to the fact that scatter correction for any detector is derived as a weighted sum of the scatter fraction from all other detector rows. The 3D scatter correction bases the scatter computation on the size of the object. This is significantly different from earlier approaches that used the path length through the object to estimate scatter fraction. The 3D scatter correction operates on the "raw" projections before the air calibration and negative log is applied to the data. This preserves the scale of the data and the approach has been found to be more effective than other approaches that were designed to be applied at a later point in data pre-processing.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method for reconstructing an image of an object; said method comprising:
    scanning the object with a computed tomography (CT) system to obtain data;
    estimating a size of the object using the obtained data;
    using the estimated size of the object to perform scatter correction on the obtained data; and
    reconstructing an image using the scatter corrected data wherein said using comprises deriving a polynomial relationship between the estimated size and an estimated detector scatter profile to obtain a scaling factor, wherein said using further comprises using the obtained scaling factor to scale the estimated detector scatter profile, wherein the estimated detector scatter profile is a square root of the obtained data after a removal of a dark current from the obtained data and a channel to channel detector gain differences normalization is performed on the obtained data.

2. A method in accordance with claim 1 wherein said estimating comprises computing an integral of the data prior to a negative log correction and an air calibration that is done to the scatter corrected data later to reconstruct the image.

3. A method in accordance with claim 1 further comprising generating a row scatter profile for each of a plurality of detector rows.

4. A method in accordance with claim 3 further comprising smoothing the detector scatter profile to eliminate high frequency changes.

5. A method in accordance with claim 4 further comprising re-introducing the channel to channel detector gain differences.

6. A method in accordance with claim 1 wherein the CT system includes a rotating gantry with a plurality of detector rows, the scan is an axial scan, and said estimating comprises estimating a size of the object during each rotation for each detector row.

7. A method for reconstructing an image of an object; said method comprising:
    scanning the object with a computed tomography (CT) system to obtain data;
    estimating a size of the object using the obtained data;
    using the estimated size of the object to perform scatter correction on the obtained data;
    reconstructing an image using the scatter corrected data wherein said using comprises deriving a polynomial relationship between the estimated size and an estimated detector scatter profile to obtain a scaling factor;
    removing channel to channel detector gain differences from the obtained data prior to performing said step of using; and
    re-introducing the channel to channel detector gain differences to the scatter corrected data.

8. A cone beam computed tomography (CT) system comprising:
    a radiation source configured to emit a cone beam of radiation;
    a detector positioned to receive the cone beam; and
    a computer coupled to said source and detector said computer configured to:
    receive data from said detector;
    estimate a size of an object using the received data;
    perform scatter correction on the received data using the estimated size of the object;
    reconstruct an image using the scatter corrected data;
    derive a polynomial relationship between the estimated size and an estimated detector scatter profile to obtain a scaling factor; and
    use the obtained scaling factor to scale the estimated detector scatter profile, wherein the estimated detector scatter profile is a square root of the obtained data after a removal of a dark current from the obtained data and a channel to channel detector gain differences normalization is performed on the obtained data.

9. A system in accordance with claim 8 wherein said computer further configured to compute an integral of the data prior to a negative log correction and an air calibration that is done to the scatter corrected data later to reconstruct the image.

10. A system in accordance with claim 8 wherein said computer further configured to generate a row scatter profile for each of a plurality of detector rows.

11. A system in accordance with claim 10 wherein said computer further configured to smooth the detector scatter profile to eliminate high frequency changes.

12. A system in accordance with claim 8 wherein said computer further configured to re-introduce the channel to channel detector gain differences.

13. A system in accordance with claim 8 wherein said computer further configured to:
    receive a bowtie filter type; and
    estimate detector scatter profile using the received filter type.

14. A computer readable medium embedded with a program configured to instruct a computer to:
- receive data from a detector;
- estimate a size of an object using the received data;
- perform scatter correction on the received data using the estimated size of the object;
- derive a polynomial relationship between the estimated size and an estimated detector scatter profile to obtain a scaling factor; and
- use the obtained scaling factor to scale the estimated detector scatter profile, wherein the estimated detector scatter profile is a square root of the obtained data after a removal of a dark current from the obtained data and a channel to channel detector gain differences normalization is performed on the obtained data.

15. A computer readable medium in accordance with claim 14 wherein said program is further configured to instruct the computer to:
- receive a bowtie filter type; and
- estimate a detector scatter profile using the received filter type.

16. A computer readable medium embedded with a program configured to instruct a computer to:
- receive a bowtie filter type; and
- estimate a detector scatter profile using the received filter type.

17. A computer readable medium embedded with a program configured to instruct a computer to z-weight a detector scatter profile to obtain a plurality of row scatter profiles.

* * * * *